United States Patent [19]

Hatschek

[11] Patent Number: 5,299,570
[45] Date of Patent: Apr. 5, 1994

[54] SYSTEM FOR MEASURING THE SATURATION OF AT LEAST ONE GAS, PARTICULARLY THE OXYGEN SATURATION OF BLOOD

[75] Inventor: Rudolf A. Hatschek, Fribourg, Switzerland

[73] Assignee: AVL Medical Instruments AG, Schaffhausen, Switzerland

[21] Appl. No.: 928,120

[22] Filed: Aug. 12, 1992

[30] Foreign Application Priority Data

Aug. 12, 1991 [CH] Switzerland ............. 2372/91-6

[51] Int. Cl.[5] ................................. A61B 5/00
[52] U.S. Cl. ........................... 128/633; 128/666; 356/41
[58] Field of Search ................. 128/633–634, 128/664–667; 250/339, 441; 356/40–41, 39

[56] References Cited

U.S. PATENT DOCUMENTS

| | | | |
|---|---|---|---|
| 4,041,932 | 8/1977 | Fostick | 128/633 |
| 4,890,619 | 1/1990 | Hatschek . | |
| 5,014,713 | 5/1991 | Roper et al. | 128/633 X |
| 5,066,859 | 11/1991 | Karkar et al. . | |
| 5,167,230 | 12/1992 | Chance | 128/633 |
| 5,190,040 | 3/1993 | Aoyagi | 128/633 |

FOREIGN PATENT DOCUMENTS 9111136 8/1991 PCT Int'l Appl. .
2228314 8/1990 United Kingdom .

OTHER PUBLICATIONS

Proceedings of the Seventh . . . ; J. C. Lin et al.: "Frontiers of Engineering . . ."; Sep. 1985, vol. 1.

Primary Examiner—Angela D. Sykes
Attorney, Agent, or Firm—Spencer, Frank & Schneider

[57] ABSTRACT

A system for measuring the saturation of at least one gas in blood has a sensor which is, intended to be placed on a living body. Light is emitted from the sensor and into the body at a light radiating zone. The sensor has a plurality of light receiving zones, serving to receive light backscattered in the body, which zones are at various distances from the light radiating zone. Light receiving means are also present, in order to measure the intensities of the light backscattered from the body and reaching the sensor in the various light receiving zones. The measuring system also has electronic circuitry, which upon measurement, based on a predetermined criterion, selects one evaluation zone from among the light receiving zones and evaluate the portion of the light detected in the evaluation range that varies periodically over time at the rate of the pulse frequency in order to detect at least one gas saturation of blood, in particular the oxygen saturation of blood.

20 Claims, 4 Drawing Sheets

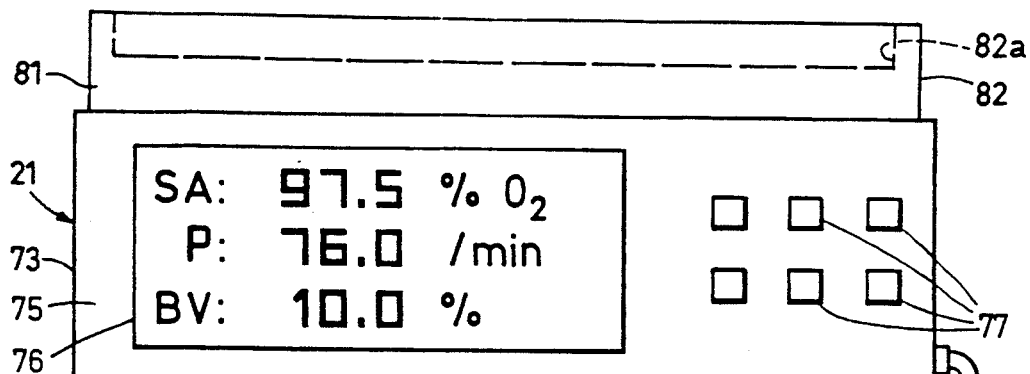
Fig.1
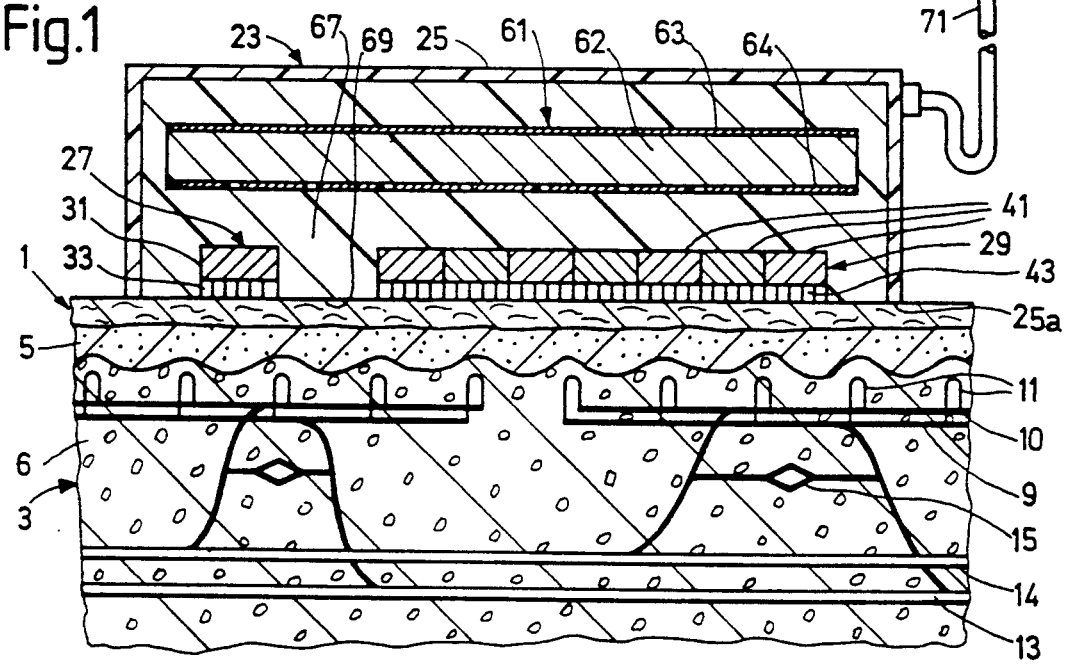
Fig.2
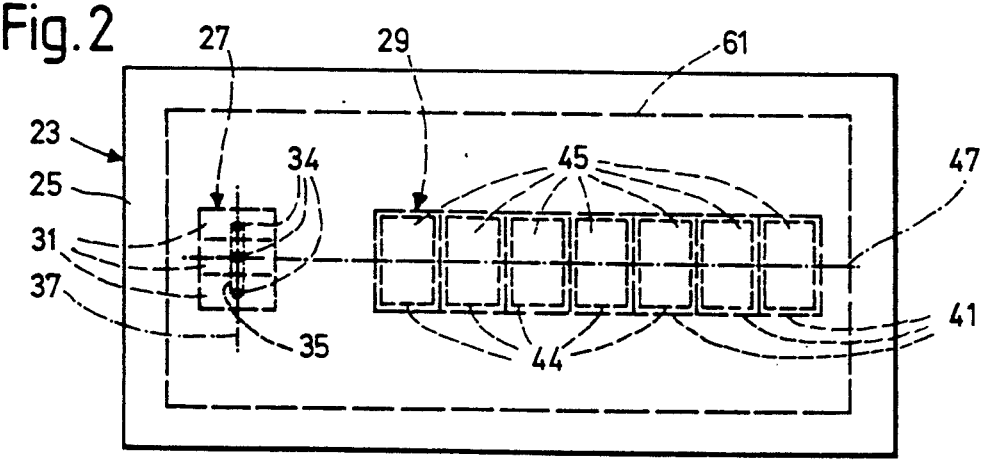

SYSTEM FOR MEASURING THE SATURATION OF AT LEAST ONE GAS, PARTICULARLY THE OXYGEN SATURATION OF BLOOD

BACKGROUND OF THE INVENTION

1. Field of the Invention

The present invention relates to a system for measuring the saturation of at least one gas, in particular the oxygen saturation, of blood present in a living body. The system may also be embodied for measuring the saturation of some other gas in blood—such as its carbon monoxide saturation, in addition to or possibly instead of measuring the oxygen saturation. The system is intended to enable noninvasive measurement. The term "noninvasive" means here that the measurement is carried out without using any instrument introduced into a blood vessel and accordingly solely with sensor means that are located entirely outside the living human or possibly animal body for which the measurement is carried out. In the planned use of the system for measuring a gas saturation, it will usually be the gas saturation of the arterial blood that is measured.

2. Description of the Prior Art

The hemoglobins present in the red blood corpuscles can bind various gases, such as oxygen and carbon monoxide—and transport them and give them up again. The blood may contain in particular oxyhemoglobin, in other words hemoglobin with bound oxygen, deoxyhemoglobin, in other words hemoglobin without oxygen, and carbon monoxide hemoglobin. The term "gas saturation" is understood as a value that provides a measure of the concentration or proportion of the hemoglobin that contains the applicable gas. For example, the oxygen saturation that is to be measured in particular may provide a measure of the ratio between the concentration of oxyhemoglobin and the concentration of the sum of the oxyhemoglobin and the deoxyhemoglobin, or of the total hemoglobin concentration. The degree of saturation that is equal to the value, shown in percentage, of the aforementioned ratio is often indicated as the measure of oxygen saturation.

For measuring the oxygen saturation or some other gas content in blood, an important factor is that light shone into a body and in particular into a blood vessel is scattered. The blood plasma and the red blood corpuscles contained in it, along with other blood cells, have various indexes of refraction, so that a beam of light upon entering a blood cell, for instance a red corpuscle, and on leaving it is normally deflected by refraction. The light can also be deflected by reflection and diffraction. The totality of all these deflection processes is called scattering. A beam of light shone into a blood vessel is typically scattered multiple times in the blood before it leaves the blood vessel again. If the light penetrates a red corpuscle, some of the light is absorbed.

In measuring the oxygen saturation using light, use is made of the fact that the hemoglobin containing bound oxygen, that is, the oxyhemoglobin, and the hemoglobin lacking oxygen, or in other words the deoxyhemoglobin, have different colors and correspondingly different light absorption spectra. If the absorption coefficients of the two types of hemoglobin are represented in the same diagram as curves as a function of the wavelength of light, the two curves intersect at so-called isobestic points, at a wavelength hereinafter called the isobestic wavelength which is approximately 805 nm.

Systems for noninvasive measurement of gas saturation in blood, in particular of its oxygen saturation, are known, for instance from the publication entitled "A New Noninvasive Back-Scattering Oximeter", by T. M. Donahoe and R. L. Longini, Proceedings of the Seventh Annual Conference of the IEEE/Engineering in Medicine and Biology Society, 1985, Chicago, Vol. 1, pp. 144–147, and U.S. Pat. No. 4,890,619 and British Patent A 2,228,314. These systems have sensor means, light transmission means in order to shine light into a body to be examined for at least one light transmission zone of the sensor means, and light reception means, in order to receive light scattered in the body in at least one light reception zone of the sensor means and measure its intensity using at least one photosemiconductor. The known systems also have electronic circuit means in order to ascertain the oxygen saturation, and possibly other variables as well, from the light intensities ascertained by the photosemiconductors.

The system known from the publication by Donahoe et al named above has two identical sensors. Each of them has two light-emitting diodes, which form light sources to generate light of two different wavelengths, and on the side of the sensor applied to the body being studied during measurement, they together define a light transmission zone through which the light generated can be shone into the body. When a measurement is carried out, one sensor, intended for measuring the oxygen saturation of the arterial blood, is heated with a heater container in it, while the other sensor is not heated and is intended to measure the oxygen saturation of the tissue.

The systems known from U.S. Pat. No. 4,890,619, already mentioned, also have two identically embodied sensors, each of which has one light receiver, embodied by a photodiode, and four or six light-emitting diodes disposed in a circle around it. The light-emitting diodes of each sensor form light sources to generate light at two different wavelengths, and together they define a circular light transmission zone in which light can be transmitted out of the sensor. The distance between the light reception zone, defined by the photodiode of the applicable sensor, and the annular light transmission zone is approximately equal to the mean radius of the light transmission zone. Some of the sensors also have ultrasound sources for heating the tissue with ultrasound. The systems known from U.S. Pat. No. 4,890,619 make it possible, depending on the arrangement of the two sensors, to measure the oxygen saturation with transmitted light passing through the body from one sensor to the other, or with backscattered light that is scattered from the body back into the same sensor in which it originated.

British Patent A 2,228,314, already mentioned, discloses a system intended, among other purposes, for measuring the oxygen saturation in the blood in the brain. The light transmission means of the system have a number of laser diodes, which are capable of generating light at various wavelengths for measuring the oxygen saturation. Each laser diode is connected to the inlet end of an optical fiber, whose outlet end is located on the surface of the head of a patient to be examined. The light reception means of the system have a number of optical fibers, with inlet ends located on the surface of the head of the patient. In the system primarily described, the optical fibers of the light reception means all lead from the head to the same single photodetector. It is also noted that a separate photodetector could be provided for each optical fiber of the light reception means, and that the computer that is part of the electronic circuitry of the system adds together the light intensities detected in measurement by the various photodetectors. The outlet ends of the optical fibers belonging to the light transmission means and the inlet ends of the optical fibers belonging to the light reception means are distributed more or less uniformly over the upper half of the head of the person to be examined. The system therefore has a number of light transmission zones and light reception zones; the light transmission zones and the light reception zones alternate along the circumference of the head, if seen in plan view vertically from above. There are also relatively large interstices between the closest-together light transmission zones and between the closest-together light reception zones. In operation of the systems, light is shone sequentially through the skull into the brain in the various light transmission zones. Light scattered there and transmitted back through the skull out of the head can then be intercepted by the various light reception zones. For example, if light is shone into the head at a light reception site located on the "equator" of the head, then at each light reception site, scattered light can be intercepted, which depending on the location of the applicable light reception site is backscattered, scattered to the side, or scattered forward.

In measurement with all the system that are known and are described above, light scattered not only by the red corpuscles but light that was scattered by dead skin cells, tissues, hair follicles, sweat glands, nerves and the like reaches the light receiver, or every light receiver. This latter light, not scattered by hemoglobins, provides no information on the oxygen saturation be measured, and it impairs the accuracy of measurement. For accurate determination of arterial oxygen saturation, the highest possible proportion of the light reaching the light receiver or receivers and evaluated to determine the oxygen saturation should therefore be scattered by the red corpuscles. As will be discussed in further detail hereinafter, the intensity of the light scattered by red corpuscles and reaching a light receiver through a light reception zone in measurement with backscattered light depends on the distance, measured along the surface of the body, of the light reception zone from the light transmission zone at which the light was shone into the body. As will also be discussed in detail hereinafter, the most favorable value for this distance depends on individual anatomical characteristics of a person being examined, on the site of the body selected for the measurement, and also on the instantaneous physiological condition of a person examined, which is subject to changes over time. The systems known from the various publications named above therefore have the disadvantages, for measurement with backscattered light, that the attainable accuracy of measurement can vary from one measurement to another, and that considerable measurement errors sometimes occur.

If the systems known from U.S. Pat. No. 4,890,619 are used to measure with transmitted light, they have not only more or less similar disadvantages to those of measurement with backscattered light, but above all the disadvantage that the measurements can be performed only on thin parts of the body, such as an earlobe or finger. In addition, measurements with transmitted light are relatively poorly suited for long-term continuous monitoring, because motion by the person being examined, for instance, often causes errors in measurement.

The situation is similar for measurements with the systems of British Patent 2,228,314. Since when these systems are operated, the light has to pass twice through bony parts of the skull, the measurable light intensities are furthermore very slight, which additionally impairs the accuracy of measurement.

In the known systems, if the intensities of transmission of the various light-emitting or laser diodes, or the sensitivity of the photosemiconductors change over the course of time, this can also impair the accuracy of measurement. In particular, inaccuracies in measurement can arise if the transmission intensity at the various wavelengths varies differently, or if the spectral sensitivity of a photosemiconductor changes.

As mentioned, the sensors of the system described in the above-named publication by Donahoe et al is equipped with a heating coil. This makes it possible to warm the skin by conduction of heat and thereby increase the circulation. If the region of the skin containing the arteries and arterioles—that is, the dermis—is warmed by heat conduction from the surface of the skin, a temperature drop from the outside inward is created in the skin. If the heating is done solely by conduction of heat, it is therefore difficult and practically impossible to heat the region of the skin containing the arteries and arterioles to an optimal temperature for measuring the arterial oxygen saturation without causing harmful overheating in certain regions of the skin.

In the sensors known from U.S. Pat. No. 4,890,619, which are equipped with ultrasound sources, there is a rather large void between the ultrasound sources, located in the interior of a housing of the sensor, and the surface of the skin of the patient being examined. For measurement this void must either be filled with a gelatinous and more or less readily flowable filling composition of polyethylene glycol, or with water, which makes the measurement process more complicated, and if water is used requires a pump for introducing it. Since the ultrasound transmitted into the skin is not uniformly absorbed there, heating that occurs solely from transmitting ultrasound into the skin, like heating effected solely by heat conduction, may also produce a temperature distribution that, while different, is still uneven.

The supply of oxygen to tissues and/or organs of a living being depends not only on the oxygen saturation of the blood but also on the intensity of blood profusion, or in other words circulation. When the oxygen saturation is measured, it is therefore desirable to measure the intensity of blood profusion at the sam=time. With the known systems used for measuring oxygen saturation, however, the blood profusion cannot be measured, or if at all, then at best with only slight accuracy.

Similar problems to those in measuring oxygen saturation can also arise when some other gas saturation is measured, such as the carbon monoxide saturation of blood.

SUMMARY OF THE INVENTION

It is therefore the object of the invention to create a system for measuring at least one gas saturation of blood—in particular its oxygen saturation—that overcomes the disadvantages of the known systems. In particular, it is an objective in measurement to attain the highest possible accuracy of measurement regardless of individual anatomical characteristics of the body of a living creature being examined, regardless of the site on the body selected for the measurement, and regardless of physiologically dictated changes in condition.

This object is attained according to the invention by providing a measuring system which includes light radiating means for generating light having various wavelengths; a sensor intended to rest on the body, the sensor having a light radiating zone where the light having various wavelengths is emitted into the body, and light receiving zones located at various distances from the light radiating zone; light receiving means for detecting the intensity of light which is scattered back by the body and which reaches each light receiving zone; and circuit means, connected to the light receiving means, for detecting the at least one gas saturation from light intensities detected for the various wavelengths, the circuit means including selection and evaluation means for selecting one evaluation zone among the light receiving zones on the basis of a predetermined criterion, and for evaluating light reaching the light receiving means only in the selected evaluation zone in order to detect the at least one gas saturation.

Scattering of the desired scattered light, which varies periodically over time at the rate of the pulse, for determining saturation of a gas—in particular oxygen—is predominantly done in the arteries present in the middle and/or deeper dermis. Contrarily, the intensity of scattered light that was scattered solely in scattering within the layers of skin located above the arteries, is predominantly constant over time and/or varies over time only more or less stochastically. The scattered light with an intensity that is constant over time and/or varies stochastically can be interpreted as the effect of background scattering or of physiological noise and can be called background—and/or noise—backscattered light. The intensity, composition and orientation of the scattered light emerging from the surface of the skin depends on the thickness, structure, and absorption characteristics of the various layers of skin, on the hematocrit and on the profusion. The hematocrit is the ratio between the volume of red corpuscles and the volume of the whole blood. It should also be noted that the hematocrit is typically expressed in percentages, and is usually approximately 42% but can vary between 20% and 60%.

The scattering taking place in the skin was investigated with model calculations and experimentally for a tightly bound beam of light shone into the skin at a punctate light transmission site. For the model calculations, the skin was divided into four layers of different scattering and absorption characteristics. Each layer was associated with the horny layer of the epidermis, the germ layer, the outer layer of the dermis, or the middle and/or deeper layer of the dermis having the arteries. In the model calculations, various models were used. In a relatively simple model, each layer was represented by a flat surface and a mathematical function that assigns a back-reflection intensity to each site on the surface. For a more complicated model that is closer to reality, the four layers were interpreted as continua and the scattering was represented and calculated by means of the diffusion of photons. Both model calculations and the experimental investigations showed that the intensity of the constant scattered light scattered back out of the skin and of the scattered light varying stochastically over time is at a maximum in the light transmission zone, and decreases with increasing distance, measured along the surface of the skin, of the light reception zone from the light transmission zone. The curve representing the course of the intensity as a function of the distance takes approximately the form of a bell curve showing a Gaussian distribution. It was also found that the intensity of the light scattered in the middle and/or deeper layer of the dermis, as well as the ratio between this intensity and the intensity of all the scattered light, first increases with increasing distance of the light reception zone from the light transmission zone and subsequently decreases again. The intensity of the light scattered in the middle and/or deeper layers of the dermis and the ratio between this intensity and the intensity of the total scattered light accordingly are at a maximum at a certain distance from the light transmission zone.

Investigation has also shown that the distances of these maxima in intensity of the light scattered in the middle and/or deeper layers of the dermis are dependent on the layer thicknesses, the depths of the arteries, the scattering and absorption characteristics of the various layers, and on the hematocrit. Since the scattering and absorption are also dependent on the profusion, or in other words on the volume of blood present in the part of the body examined, the location of the maxima may also be dependent on the profusion. Since the thicknesses of the various layers of skin, the scattering and absorption characteristics, and the hematocrit can also vary from one individual to another, are dependent on the site on the body selected for measurement, and sometimes can even change over time, the distances at which the aforementioned maxima occur are also various.

According to the invention the system therefore has a sensor with a plurality of light reception or receiving zones in which the light intensities can be measured separately. In a plan view on the side of the sensor intended for application to a living body, and accordingly measured along the body surface on which the sensor rests in measurement, the light reception zones are at various distances from the light transmission zone of the sensor.

The system according to the invention also has circuit means, namely electronic circuit means, which selects at least one favorable light reception zone as an evaluation zone on the basis of a predetermined selection criterion. For example, the circuit means, which may for instance have a microprocessor, may be embodied to detect the pulse frequency and to use the portion of the scattered light that varies periodically at the rate of the pulse to determine the gas saturation—for example the oxygen saturation—of the hemoglobins in the arterial blood. The circuit means can then ascertain the gas saturation, for instance, from the light intensities measured in the particular light reception zone in which the rise and hence the amplitude of the light intensity, varying at the rate of the heart beats, is the highest for one of the light wavelengths used, or in which the ratio between the aforementioned amplitude and the intensity of the total scattered light having the aforementioned wavelength are highest.

BRIEF DESCRIPTION OF THE DRAWINGS

The invention will be better understood and objects other than those set forth above will become apparent from the ensuing detailed description of exemplary embodiments thereof, taken in conjunction with the drawings, wherein:

FIG. 1 is a schematic section, not to scale, through a part of the skin of a living body and a system for measuring the oxygen saturation, using a sensor shown in section and applied to the skin, and a measuring device connected to the sensor and shown in a front view;

FIG. 2 is a plan view of the sensor that can be seen in FIG. 1;

DETAILED DESCRIPTION OF THE PREFERRED EMBODIMENTS

Figure 3:
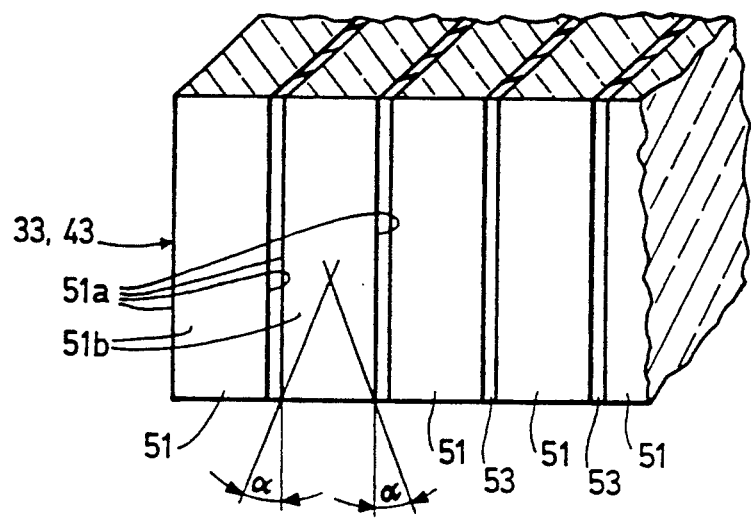
FIG. 3 is an axonometric view of a detail of the light guide means present in the sensor, on a substantially larger scale than the sensors shown in FIGS. 1 and 2

In FIG. 1, part of the skin 3 belonging to the body 1 of a patient can be seen. This part comprises the epidermis 5, which lacks blood vessels, and the dermis 6 containing the blood vessels. The epidermis 5 can be subdivided into at least two layers, namely the horny layer and the germ layer, of which the horny layer, made up of dead cells, forms the surface of the body 1. The outer or upper layer of the dermis 6 contains the smallest blood vessels, which enable microscopic circulation, namely arterioles 9, venules 10 and capillary loops 11. The arterioles 9 and venules 10 are connected to larger arteries 13 and veins 14 located in the middle and/or deeper layers of the dermis 6. The dermis also includes arteriovenous anastomoses 15, which form the controllable connections between an arteriole and a venule, serve to control profusion, and in the open state are capable of bridging the capillary vessels connected to the applicable arterioles.

FIG. 1 also shows a system, identified in general by reference numeral 21, for measuring a saturation of at least one gas in blood, namely at least the oxygen saturation in blood. The system 21 has sensor means with one and only one sensor 23, which when it is moistened is applied to the surface of the skin 3. The sensor may be selectively disposed at a number of different sites on the body. The sensor 23 can be detachably secured to the skin 3 with fastening means, not shown—such as at least one adhesive tape.

The substantially dimensionally stable sensor 23 also shown separately in FIG. 2 has a housing 25, which is approximately in the form of an elongated parallelepiped for instance, but may have rounded transitions instead of sharp corners. The housing 25, which for instance is of plastic, is open on its side oriented toward the skin 3 in measurement, and there has an encompassing housing rim 25a, which defines a flat surface. The housing is closed on all of its other sides.

Light transmission means or light radiating means 27 and light reception means or light receiving means 29 are disposed in the housing. The light transmission means 27 have a plurality of light sources 31, specifically three of them. They are embodied by semiconductor diodes, in other words by light-emitting diodes for generating "conventional" light, or at least some of them may be laser diodes to generate light that is coherent both three-dimensionally and chronologically, and they may for instance gallium aluminum arsenic (GaAlAs) diodes. Each of the three semiconductor diodes has a light-emitting site turned toward the skin 3 in measurement, and in operation it produces a beam of light the opening or cone angle of which is approximately 10° at most, for example, and whose diameter at the light emitting site of the diode is at most or approximately 0.2 mm, for example. Each of the three light sources 31 or diodes may generate pulsed light that is at least approximately monochromatic and for example is coherent. However, the three light sources 31 are embodied to generate three different types of light, each of which has a different wavelength from the others. The three light sources 31 are hereinafter called the first, second and third light sources; this numbering may, for example, match the order counted from top to bottom in FIG. 2, but this is not absolutely necessary. The first light source may generate light having a wavelength in the vicinity of the isobestic wavelength, such as approximately 800 to 830 nm. The other two light sources may then generate types of light whose wavelengths differ by at least 100 nm from the isobestic wavelengths, specifically being less than that wavelength. The second light source can preferably generate light whose wavelength is in the range from approximately 620 nm to 750 nm, in which the coefficients of absorption of oxyhemoglobin and deoxyhemoglobin are markedly different from one another. For example, the second light source may generate light at a wavelength of approximately 660 nm. The third light source can then generate light whose wavelength is in the range from approximately 500 nm to 600 nm, in which both oxyhemoglobin and deoxyhemoglobin, as well as hemoglobin with bound carbon monoxide, exhibit relatively high absorption. The wavelength of the light generated by the third light source may for instance be approximately 575 nm.

The three light sources 31 or semiconductor diodes each comprise a separate component area and are disposed in a straight line as close together as possible, so that they at least approximately touch one another in pairs. The light sources 31 also have a generally quadrilateral, specifically rectangular outline, for example, with the longer sides of the rectangle extending at right angles to a straight line 37 that is at right angles to the lengthwise direction of the housing 25. The light transmission means 27 also have light guide means 33, which comprise a chip-like body that is common to all the light sources 31 and will be described in further detail hereinafter. The light guide means 33 have a flat light entry face oriented toward and resting on the light sources 31 and a flat light exit face, which is located at least approximately and specifically precisely in the plane defined by the rim 25a of the housing 25. The three light sources 31, in a plan view on this light exit face, each define a light transmission or light radiating site 34, in which the light generated by the applicable light source during operation is transmitted out of the sensor, and which by way of example comprises a small, circular almost punctate field. The three light transmission sites 34 are surrounded by an envelope line which defines an approximately rectangular light transmission or light radiating zone 35. The center points of the light transmission sites 34 defined in the aforementioned plan view by the three semiconductor diodes 31 are located on the straight line 37. The center point of the middle light transmission site 34 also forms the center point of the entire light transmission zone 35. The dimensions of the light sources 31 measured along the straight line 37 and the distances between the center points of the adjacent light transmission sites 34 are preferably at most 2 mm, and for example approximately 1 mm to 1.5 mm. The length of the light transmission zone 35 measured along the straight line 37 is accordingly at most 6 mm and preferably at most 5 mm. The length of the light transmission zone 35 measured at right angles to the straight line 37 is at most 2 mm, preferably at most 1 mm, and for example less than 0.5 mm.

The light reception means 29 have a plurality of light receivers 41 disposed in a straight row, specifically at least three of them, preferably at least 5, and for example up to approximately 20; for the exemplary embodiment, seven light receivers have been shown. They comprise separate, identically embodied photosemiconductors, namely silicon photodiodes. The light reception means 29 are equipped with light guide means 43, which comprise one chip-like body common to all the light receivers 41, which for each light receiver forms one multiple optical fiber and non-projecting collimator associated with that light receiver. The light guide means 43 have a flat light entry face, which is located at least approximately and specifically precisely in the plane defined by the rim 25a of the housing 25, and a flat light exit face, which is turned toward the light entry sides of the light receivers 41 and rests on them.

The light receivers 41 are disposed at least approximately without gaps side by side along the line formed by them. Seen in plan view, each light receiver 41 defines a light admission field 44 on the side of the sensor that rests on the body in measurement and accordingly in the light entry face of the light guide means 43; in this field, light can pass through the light guide means 43 into the applicable light receiver, so that this light receiver can then measure the intensity of that light. The light admission fields 44 form a straight line corresponding to the arrangement of light receivers 41 and have center points located on a straight center line 47. The center line 47 extends parallel to the lengthwise direction of the housing 25 and at right angles to the straight line 37 through the center point of the middle light transmission site 34 and of the entire light transmission zone 35. The light admission fields 44 have a generally quadrilateral and specifically rectangular outline in general, with the longer sides of the rectangle parallel to the straight line 37. The light admission fields 44 of the light receivers that are adjacent to one another in pairs follow one another at least approximately without gaps. Depending on the embodiment of the housing and of the light entry sides of the light receivers 41, however, there may be small interstices—that is, surface segments—between the adjacent pairs of light admission fields 44, in which interstices the light striking them reaches none of the light receivers. The length of each light admission field 44, measured lengthwise of the line of light receivers, should be more than half and preferably at least two thirds the distance between the center points of adjacent light admission fields 44, however. Each of these fields serves as a light reception zone or light receiving zones 45, in which, during operation, the intensity of the light backscattered in the body 1 and reaching the sensor again can be measured separately.

The various light admission fields 4 and the light reception zones 45 identical with them have different spacings from the light transmission sites 34, from the light transmission zone 35 containing them and from the straight line 37 extending through the center points of the light transmission sites 34 It should be noted that these distances are measured at right angles to the center axes of the beams of light transmitted out of the sensor 23 at the light transmission sites 34, in parallel to the plane in which the light transmission sites 34, the light transmission zones 35 and the light reception zones 45 are located. The distance between the center point of the light admission field 44 or light reception zone 45 closest to the light transmission zone 35 and the straight line 37 and from the center point of the light transmission zone 35 is preferably at least 4 mm, preferably at most 10 mm, and for example approximately 7 mm. The dimensions of the light receivers 41 and light admission fields 44 measured parallel to the straight line 47, and the spacings of the center points of adjacent light admission fields 44 or light reception zones 45, are preferably at most 3 mm and for example are 1.5 mm to 2.5 mm. The distance from the center point of the light admission field 44 or light reception zone 45 located farthest away from the light transmission site 44 from the straight line 37 and from the center point of the light transmission zone 35 is preferably at least 15 mm, and for example 18 mm to 30 mm. The dimension—that is length—for each light admission field 44 measured parallel to the straight line 37 is preferably approximately the same as or at least equal to the dimension measured in the same direction measured of the light transmission zone 35, or in other words of the line formed by the three light transmission sites 34.

The two chip-like bodies forming the light guide means 33 and 43 have approximately or precisely the same shapes and dimensions in outline, in the plan view shown in FIG. 2, as the group of light sources 31 or the group of light receivers 41. Furthermore, the light guide means 3 and 43 are embodied identically or similarly, aside from their different shapes and dimensions in outline.

The embodiment of the light guide means will now be described in conjunction with FIG. 3, which is a detail of one of the light guide means. The photoconductive means have a number of flat plates 51 of rectangular outline, which are parallel to one another and perpendicular to the straight line 47. The faces of the plates present on the broadsides of the plates 51 are marked 51a. The succeeding plates 51 along the straight line 47 are firmly joined together by layers 53 disposed between the faces 51a of each pair of plates facing toward one another. On all sides, the plates 51 have flat peripheral faces at right angles to the planes of the plates. The plates 51 are of clear glass and as transparent as possible for the three types of light generated, and comprise a mineral glass, for example.

The flat peripheral faces of the plates 51 of the light guide means 33 oriented toward the light sources 31 together form the light entry face of these light guide means. The flat peripheral faces of the plates 51 of the light guide means 33 remote from the light sources 31 together form the light exit face of the light sources, and this face contains the light transmission sites 34 and the light transmission zone 35. It should be noted that the diameters of the beams of light generated by the light sources 31 are substantially smaller than the dimensions of the light guide means 33 measured parallel to the straight line 47, so that light is in fact passed through only some of the plates 51 belonging to them, or through even only a single plate 51 of the light guide mean 33. The peripheral faces of the plates of the light guide means 43 remote from the light receivers 41 together form their light entry face, the light admission fields 44 and the light reception zones 45. The peripheral faces of the plates of the light guide means 43 oriented toward the light receivers 41 form their light exit face.

The layers 53 are formed of a material that at least partly comprises an adhesive that is more or less highly transparent and has a lower coefficient of diffraction than the glass forming the plate 51. The adhesive may for example be embodied by a two- component adhesive, one component of which is an epoxy resin. In the light guide means 43, those layers 53 that form the boundary between different light admission fields 44, may possibly also contain highly light-absorbent particles disposed in the epoxy resin that forms a transparent matrix. If necessary, all the layers 53 of the light guide means 33 and 43 may even contain such particles. These particles increase the light absorption of the layers 53 and make them more or less opaque. Moreover, the faces 51a of the plates 51 located at the ends remote from one another of the rows of plates of the light guide means 33, 43, and the peripheral faces 51b of the plates at right angles to the light inlet faces and light exit faces of the light guide means 33, 43, may optionally also be provided with a coating which is of the same material as the layers 53. The option also exists of providing these last-named peripheral faces of the plates with a coating that provides mirroring and may comprise a sputter-deposited metal film. The light guide means 33, 43 are also electrically insulating.

The thickness of each plate 51, measured parallel to the straight line 47, is substantially less than the length measured in the same direction of each light admission field 44 and each light reception zone 45. In addition, the thickness of each plate 51 is less than the height of the light guide means, measured at right angles to the light inlet and exit faces of these light guide means. For instance, the thickness of the plates 51 may be approximately 0.15 mm to 0.25 mm. The height of the plates and of the entire light guide means may be approximately 1 mm to 2 mm. The thickness of the layers 53 is preferably at most 30% and for example approximately or at most 20% the thickness of the plates 51.

If light, which has reached the inside of a plate 51 through the light entry face of the light guide means 33 or 43, passes from the interior of the plate to one of its faces 51a that forms an optical boundary between the applicable plate 51 and a layer 53, this light is reflected in toto or only in part—depending on the angle between the boundary and the light striking the boundary. Total reflection occurs only whenever the aforementioned angle is equal to or less than the boundary value of the angle limit value $\alpha$ in FIG. 3. This value is determined by the ratio between the indexes of refraction of the glass forming the disks and of the material forming the layers 53, and it may for instance be defined such that it amounts to at most 45° or at most 30° or at most 20°. The center plane of the light guide means 33 and/or 43 is understood hereinafter to be the plane that is perpendicular to the flat light entry and light exit faces and extends through the straight light 47. Light that is transmitted into a plate 51 parallel to the aforementioned center plane and forms an angle with the faces 51 that is at most equal to the angle limit value $\alpha$ can pass through the disk without significant attenuation. Contrarily, light that is propagated parallel to the aforementioned center plane but forms an angle larger than $\alpha$ with the faces 51a is attenuated more or less markedly. The plates 51 in cooperation with the layers 53 accordingly form optical wave guides; in addition—at least for light oriented parallel to the aforementioned center plane—they effect focusing, or in other words a nonprojecting collimation. Because of this collimation, only light whose orientation is in an angular range of 2$\alpha$ passes unattenuated through the light guide means. Contrarily, light that is perpendicular to the straight line 47 and accordingly has propagation directions parallel to the plates 51 can pass through the light guide means practically without attenuation, even if it forms a large angle with a straight line that is vertical to the surface of the skin. The light guide means has a large transmissive cross-sectional area for the light. It should also be noted in this respect that the collimating action for the light guide means 33 located in front of the light sources 31 is intrinsically unessential, because the light sources 31 already produce concentrated beams of light with nearly parallel light rays.

To manufacture the light guide means 33 and 43, it is possible, for instance by cementing glass plates together, to form blocks that in outline have the shapes and dimensions of the light transmission means 27 and light reception means 29 shown in FIG. 2, and that have a height that is a multiple of the height visible in FIG. 1 of the finished light guide means. Chip-like bodies having the height intended for the light guide means can then be cut from these blocks.

Figure 4:
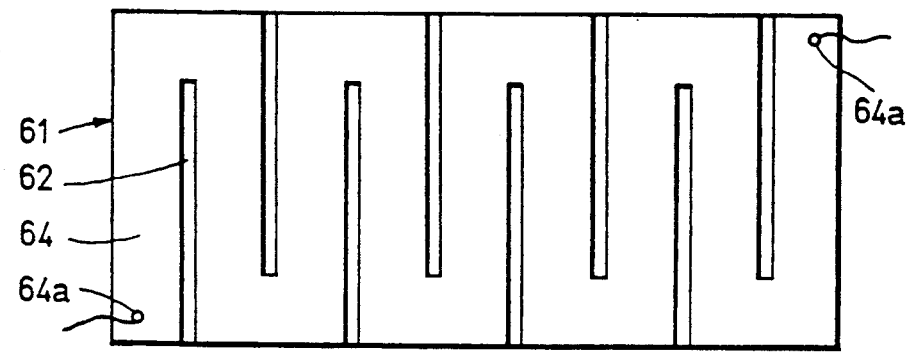
FIG. 4 is a front view of the electrode located in FIG. 1 on the lower end of the piezoelectric element in the sensor.

In the housing 25, an ultrasound source 61 shown separately in FIG. 4 is disposed on the side of the light sources 31 and light receivers 41 remote from the light transmission zone 35 and the light admission fields 44 and light reception zones 45. The ultrasound source comprises a piezoelectric element 62, which takes the form of a rectangular chip, and two electrodes 63, 64 disposed on sides of this element remote from one another. The piezoelectric element 62, in the projection at right angles to the light reception zones shown in FIG. 2, protrudes past the light transmission zone 35 and the light reception zones 45 to all sides. At least one of the electrodes 63, 64, namely, for example, the electrode 63 located on the side of the piezoelectric element 62 remote from the light sources 31 and light receivers 41, is rectangular, as is the element 62, and it covers the element 62 completely. The electrode 64 that can also be seen in FIG. 4, located on the side of the piezoelectric element 62 toward the light sources 31 and light receivers 41, is formed by an elongated wave- shaped and/or meandering strip, which covers the great majority of the element 62 but simultaneously forms an electrical resistor that can be used as a temperature sensor and is provided with a terminal 64a on both ends. The electrode 63, like the element 62, is rectangular and covers the latter completely, but could also have a corrugated and/or meander shape and serve as a temperature sensor.

Ultrasound transmission means are also present, for transmitting ultrasound waves, generated by the ultrasound source 61 during operation, to the skin 3 of the body 1. These ultrasound transmission means have a fixed ultrasound transmission and heating body 67 The heating body 67 is formed by a casting resin poured into the housing 75; it surrounds the ultrasound source 61 on all sides, together with it and with the various parts of the light transmitting means and light reception means it forms a solid, compact block that fills all the voids in the housing completely and without pores, and extends up to the plane defined by the rim 25a of the housing 25. On its side intended to rest on the living body 1, the sensor 23 therefore has a flat, smooth and compact—recess-free—limiting or contact face 69, which is formed by the housing rim 25a, the light guide means 33, 43 and the ultrasound transmission and heating body 67, and which contains and completely surrounds the light transmission zone 35 with all the light transmission sites 34 as well as all the light admission fields 44 and light reception zones 45. Before the sensor 23 is used, a thin, gelatinous or in other words semisolid/semifluid ultrasound transmission layer, not shown, comprising polyethylene glycol, for instance, and transparent to the light used for the measurement, is applied to the limiting and/or contact face 69 of the sensor intended for application to the body 1; this layer covers the face 69 completely and has a thickness of 0.001 mm to 0.01 mm, for instance. The aforementioned block, formed by the ultrasound transmission and heating body 67, the light transmission means 27, the light reception means 29, and the ultrasound source 61, along with the gelatinous ultrasound transmission layer, enables good adaptation of the ultrasound wave resistance of the ultrasound source 61 to that of the skin 3, so that ultrasound waves generated by the ultrasound source 61 can be transmitted to the skin 3 of the body 1 with as few reflections as possible. The ultrasound transmission and heating body 67 is moreover embodied such that it absorbs some of the energy generated by the ultrasound source in the form of ultrasound waves and converts it into heat. As a result, during operation, the ultrasound transmission and heating body 67 can be warmed to a regulatable temperature that for instance is in the range from 37° C. to 43° C.

The light sources 31, light receivers 41 and the electrodes 63, 64 of the sensor 23 are electrically connected, via a flexible cable 71, to a measuring instrument disposed at some distance from the person being examined. This instrument comprises a unit with a housing 75, on and/or in which a display device 76 and manually actuatable switching and/or control devices are secured.

Figure 5:
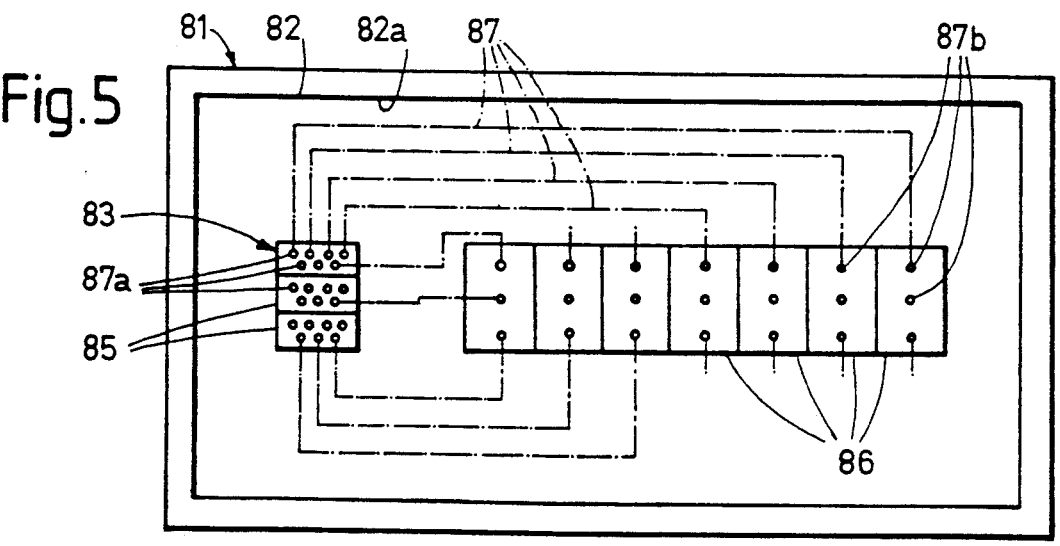
FIG. 5 is a simplified front view of the side of the calibration light distributor of the system intended to be turned toward the sensor.

The system 21 has a calibration light distributor 81, shown in FIG. 1 and separately in FIG. 5. The calibration light distributor 81 has a support 82, which is secured for instance to the top of the housing 75 in such a way that it is accessible from the area around this housing. The support 82 is embodied such that the sensor 23, if it is not being used for measurement, and in particular for calibration, can be temporarily disposed in a defined position on and/or in the support 82 and inserted into an indentation 82a on the support, for instance, and optionally can be detachably secured with any arbitrary fasteners, not shown, such as detent means.

The calibration light distributor 81 is provided with light distributing means 83 in order, upon calibration of the various light sources 31 of the sensor 23, to distribute light, generated and transmitted from the sensor in the light transmission sites 34 to the various light admission fields 44 or light reception zones 45 in a predetermined manner and deliver it there to the light receivers 41. The light distributing means 83 have one light coupling element 85, for instance, for each light transmission site 34 belonging to the sensor 23, the light coupling element being opposite the light transmission site during calibration, and for each light reception zone 45 belonging to the sensor 23, it may have one light coupling element 86 located opposite that zone in calibration, as well as a number of optical waveguides 87, each with one glass fiber, only some of which are shown in FIG. 5. Each optical waveguide 87 has one end 87a connected to a light coupling element 85 and one end 87b connected to a light coupling element 86. The light coupling elements 85, 86 may each have one light-transmissive, and for instance glass-clear body, which is for instance formed from a cast resin and is cast onto a group of waveguide ends 87a or 87b. Each light coupling element 85 is connected with each light coupling element 86 by means of at least one, and preferably more than one, optical waveguide 87. Preferably, all the pairs of light coupling elements 85, 86 are joined together by the same number of optical waveguides.

Figure 6:
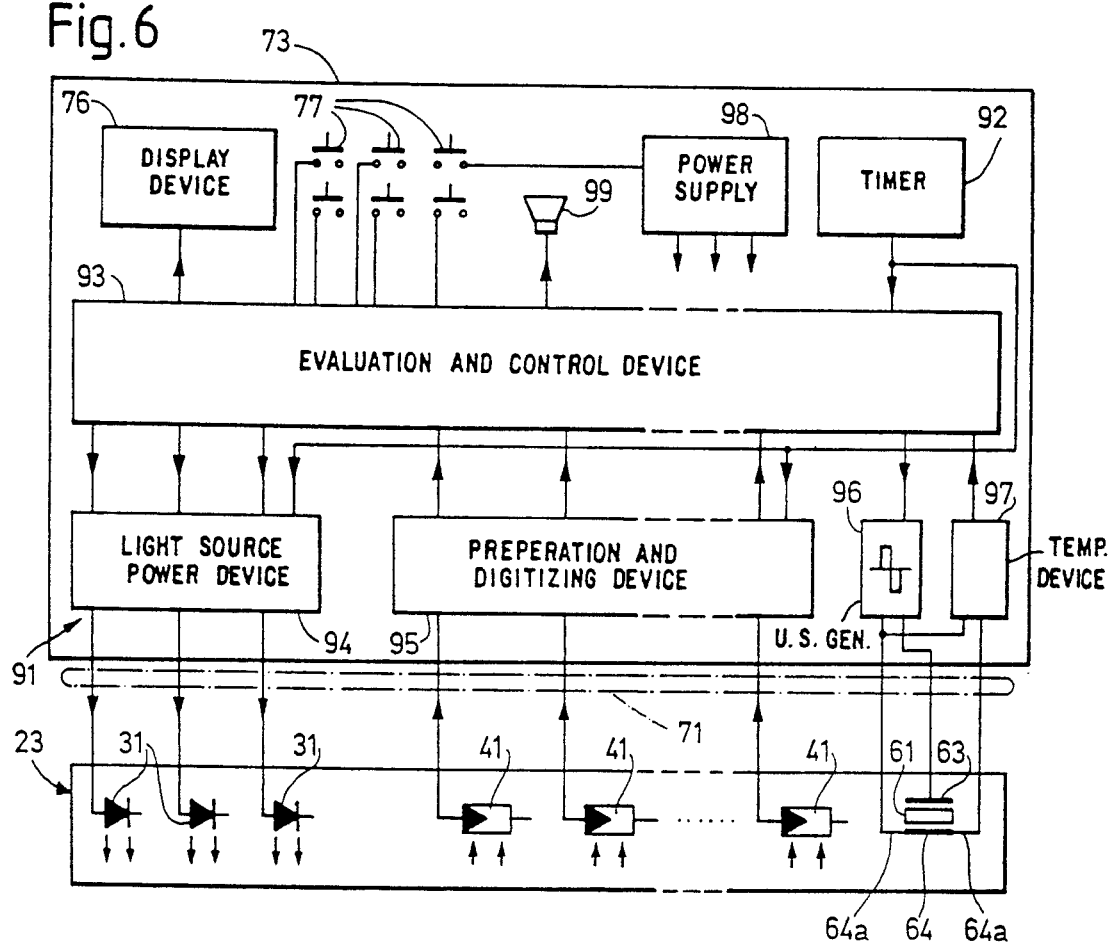
FIG. 6 is a block circuit diagram of the system shown in FIG. 1.

Electronic circuit means 91, whose block circuit diagram is found in FIG. 6, are accommodated in the housing 75 of the measuring instrument 73. The circuit means 91 have a timer 92, for instance, and an evaluation and control device 93, which is at least partly formed by a microprocessor connected to the timer. A light source power device 94 has inputs connected to both the timer 92 and the device 93 as well as outputs connected to the light sources 31 of the sensor 23 via the cable 71. The light receivers 41 of the sensor 23 are connected via the cable 71 to inputs of a preparation and digitizing device 95 belonging to the circuit means 91., the device 95 also has an input connected to the timer 92 and outputs connected to the device 93. An ultrasound generator 96 has at least one input connected to the evaluation and control device 93, as well as outputs connected via the cable 71 to the electrodes 63 and to one terminal 64a of the electrode 64. This terminal 64a and the other terminal 64a of the electrode 64, which also acts as a temperature sensor are also connected to a temperature measuring device 97, which in turn is also connected to the evaluation and control device 93. One of the manually actuatable switch and/or control devices 77 serves as an on and off switch and is connected to a power supply 98, which supplies the remaining devices of the circuit means 91 with the voltages required for their operation. At least some of the other switch and/or control devices 77 are connected to the evaluation and control device 93. An acoustic alarm 99 may also be present, connected to the device 93.

The operation of the system 21 will now be described. For the purposes of this description, it is assumed that the system is calibrated, and that the sensor 23 rests on the surface of the body 1 as shown in FIG. 1 and is secured detachably to it with adhesive tape or in some other way. The aforementioned thin ultrasound transmission layer of gelatinous polyethylene glycol is also present between the sensor 23 and the surface of the skin, but there are known interstices there that contain air.

When the measuring instrument 73 is turned on, the evaluation and control device 93 controls the light source power device 94 in such a way that it delivers pulse trains chronologically offset from one another to the three light sources 31, so that these three light sources 31 generate light pulses cyclically. The frequency of these pulse trains is substantially greater than the pulse or heartbeat frequency and is at least approximately 100 Hz, and for example is 1 kHz to 5 kHz. The various light pulses are intended to have a duration of less than one-third the period or cycle time and to be distributed chronologically such that at any moment, only light of a single wavelength is being generated. The light pulses generated are then transmitted out of the sensor 23 through the light guide means 33 at the light transmission sites 34 and into the skin 3 of the body 1.

The flow of the blood flowing through an artery 13 located in the middle or deeper epidermis is markedly pulsating; naturally, the pulsation is at the rate of the heartbeats or pulse. Contrarily, in the arterioles 9 located in the outer or upper dermis, the blood flow pulsates at most only slightly and in the capillary loops 11, venules 10 and in the veins 14, it is practically uniform. The light at the wavelength indicated that is shone into the skin 3 can penetrate as far as the middle and/or deeper layer of the dermis 6, and in particular into the blood vessels present there as well. As discussed in the introduction, the light in the blood penetrates red corpuscles and other blood cells and in the process is deflected by multiple scattering above all by the processes of refraction. The red blood corpuscles absorb some of the light, the absorption being dependent on the wavelength of the light and on whether or not the hemoglobin of the corpuscles contains oxygen. Some of the light deflected by corpuscles can than be scattered back to the surface of the skin 3 and in the light admission fields 44 or light reception zones 45 can enter the light guide means and pass through them into the light receivers 41.

The intensity of the light that is scattered by blood which is flowing with pulsation through the arteries 13 located in the middle or deeper layer of the dermis pulsates at the rate of the pulse or heartbeat frequency. This is true for the light of all three types, or in other words the light at all three wavelengths. As already described in the introduction, however, the light shone into the skin 3 is not scattered only by the pulsating blood flowing through at least one artery 13. In fact, the light is already scattered in the epidermis 5, in particular in the horny layer made up of dead cells. In the dermis 6, the tissue, hair follicles, sweat glands, nerves, the blood pulsating only slightly as it flows through the arterioles 9, and the practically nonpulsating blood flowing through the capillary loops 11, venules 10 and veins 4, also cause scattering of the light shone in. It is therefore also possible for scattered light whose intensity does not pulsate to reach the light admission fields 44 or light reception zones 45 and the light receivers 41.

The light receivers 41 convert the light pulses reaching them into electrical signals, namely voltage pulses, whose level provides a measure of the intensity of the light reaching the light receivers. The electrical signals, or in other words voltage pulses, generated by the light receivers are then delivered to the preparation and digitizing device 95. Upon each light pulse, this device generates an electrical signal, which in digital form gives a measure of the light intensity. The signals generated by the preparation and digitizing device 95 are then delivered to the evaluation and control device 93.

The light reaching the light receivers 41 includes a nonpulsating portion, in other words one which is constant over time, a portion which varies periodically at the rate of the pulse or heartbeat frequency, and yet another portion that varies irregularly, or in other words more or less stochastically and not periodically, which is typically called physiological noise. To determine the oxygen saturation and other variables of interest, the portions that pulsate at the rate of the pulse or heartbeat frequency of the types of light having the three different wavelengths are used. The evaluation and control device 93 is embodied so as to assign the light pulses received by each light receiver to the three wavelengths on the basis of the time of their arrival.

The device 93 is furthermore embodied such that in operation, in cooperation with the preparation and digitizing device 95, it also determines both the pulse period duration and the pulse frequency and performs the function of a digital cumulative filter. For cumulative filtering, the device 93 may for instance divide each pulse period duration into a number of time intervals of equal length. The division into time intervals is preferably triggered by the intensity maximum that is least influenced by noise. The device 93 also has a memory in which for each light receiver, one memory location is assigned to each of the aforementioned intervals. The measured values can then be stored separately in the memory locations during a predetermined number of successive pulse periods for each light receiver 41 and accumulated in each pulse period or in other words added together.

Since the periodically varying portion of the light intensity within a certain time interval has the same value in each measurement, while the value of the noise signal occurring in the applicable time interval varies stochastically from one period to another, the ratio between the value of the periodically varying signal and the value of the noise signal is increased by the accumulation. The accumulation may be carried out as a function of the noise component and of the desired measurement accuracy, for instance over the course of approximately five to one hundred heartbeats.

Once the accumulation process has been carried out for the intended number of periods, the values stored in memory for each light receiver 43 represent three stairstep curves. Each of them in turn represents the course over time extending over the length of a period of the intensity of one type of light, which has one of the three wavelengths. The evaluation and control device 93 also determines, for each of these stairstep curves, the rise of the periodically varying, cumulative light intensity, or in other words the difference between the maximum and minimum values of the cumulative light intensity represented by one stairstep curve. Once n accumulations have been carried out, this difference is equal to 2n times the amplitude of the periodically varying portion of the light intensity and accordingly provides a measure of the amplitude of this periodically varying portion of the light intensity.

From the rises or amplitudes of the light at a wavelength of 800 to 830 nm and of the light at a wavelength of approximately 660 nm, the evaluation and control device 93 can ascertain the oxygen saturation.

To explain the detection of the oxygen saturation by this system according to the invention, some details of the scattering and absorption processes that take place in the skin and of the measuring process will now be described in detail as well. The beams of light generated by the light sources 31 and passing through the light guide means 33 have center axes upon emerging from the sensors that are at least approximately perpendicular to the surface of the skin. The light guide means 33 at least predominantly assure that light generated by the light sources 31 cannot reach the regions of the skin that are part of the epidermis 5 or dermis 6, which looking in the direction perpendicular to the skin surface are located immediately in front of the light reception zones 45, without at least one scattering process that takes place inside the skin. In this respect, it should also be noted in connection with FIG. 1 that there the skin 3 has been shown with a greatly exaggerated thickness in comparison with the distances between the light receivers 41 and the light sources 31. The light guide means 33 disposed between the light sources 31 and the skin 3 insulate the skin 3 electrically as well as to a certain extent thermally from the light sources 31, so that the skin is not damaged by the heat generated by the light emitted diodes.

As described in the background section, the intensity of the light that is scattered in the middle and/or deeper layer of the dermis by pulsating blood flowing through at least one artery 13 and that emerges from the skin again is at a maximum at a certain distance from the light transmitting zone 35. This distance is dependent on anatomical characteristics—such as the thickness and structure of the various skin layers, the depth of the arteries 13, and the hematocrit—and accordingly on individual characteristics of the person being examined and on the measurement site selected. The distance is also dependent on variables that vary over time, such as the aforementioned hematocrit and the profusion., the latter can be affected by the muscle fibers in the walls of the arteries 13 and by the anastomoses 15, among other factors.

The light scattered back to the surface of the skin can emerge from the skin in various directions. Of the scattered light, whose orientations are parallel to the sectional plane of FIG. 1, only that light which with a straight line perpendicular to the skin surface forms an angle that is at most equal to the selected angle limit value $a$, and accordingly is at most 20°, for example, is allowed by the light guide means 43 disposed in front of the light receivers 41 and forming the light admission fields 44 and light reception regions 45 to reach the light receivers. The light guide means 43 therefore contribute to the fact that especially in relatively deep layers of the skin 3, scattered light reaches the light receivers 41. The light guide means 43 also insulate the skin 3 electrically and to a certain extent thermally from the light receivers 41.

The microprocessor of the evaluation and control device 93 is embodied and programmed such that it detects the light receiver in which the light intensities meet a predetermined selection criterion. For example, the microprocessor can detect the light receiver in which the amplitude of the periodically varying portion of the light having the wave length amounting to 800 nm to 830 nm, and accordingly located in the vicinity of the isobestic wave length, is at a maximum. The microprocessor then evaluates solely the light intensities, measured by that light receiver and represented by electrical signals and pulsating at the rate of the pulse frequency, to detect the oxygen saturation. Hence the microprocessor selects the light admission field 44 located in front of the applicable light receiver, or the light reception zone 45 identical to this field, as an evaluation zone and to measure the oxygen saturation evaluates only the light reaching the sensor in that zone.

Instead, however, it is possible as noted in the introduction for the signals of the light receiver in which a ratio is at a maximum may be evaluated to determine the oxygen saturation. The ratio that is employed may be the ratio between the amplitude (at a light receiver) of the periodically varying portion of the light having approximately the isobestic wave length and the maximum value of the total light having approximately the isobestic wave length, or the ratio between the amplitude of the periodically varying portion of the light having approximately the isobestic wave length and the mean value or the minimum value of the total light having approximately the isobestic wave length. It should be noted that normally all these various selection criteria are met for one and the same light receiver.

Under some circumstances, the most favorable light reception site may be located approximately in the middle between two adjacent light admission fields 44 or light reception zones 45, so that the predetermined selection criterion is met approximately equally well for two like admission fields 44. It may possibly even happen that approximately optimal measuring conditions prevail for more than two, for instance three, light admission fields 44. The microprocessor can then optionally be embodied and programmed such that in that kind of case, it adds together the light intensities measured from two or even more light receivers for every type of light or in other words wavelength, and evaluates them to determine the oxygen saturation. This means that to determine the oxygen saturation, an evaluation range which includes two or optionally even more light admission fields 44 or light reception zones 45 succeeding one another along the straight line 47 is selected or determined. The size of the evaluation range in which the light reaching the sensor is used to measure the saturation can accordingly be electronically varied to some extent. However, normally, only the light reaching the sensor through some of the light admission fields is ever evaluated to determine the oxygen saturation, and never the light reaching the sensor through all the light admission fields 44.

By the elimination of undesirable scattered light, which is achieved with the light guide means 33, 43, and by the selection as described of at least one favorable light receiver 41 and at least one favorable light reception zone associated with it for detecting the oxygen saturation, it can be attained that in all the measurements, a large amount of light that periodically varies over time at the rate of the pulse or heartbeat and that is scattered by arterial blood reaches the selected light receiver. This in turn assures high accuracy of measurement.

The ultrasound source 61 generates ultrasound waves in pulses during the measuring processes and optionally even before the actual commencement of measurement. Some of the wave energy is absorbed by the ultrasound transmission and heating body 67 and converted into heat. The portion of energy converted into heat preferably amounts to approximately 30% to 70% of the total energy supplied, in the form of ultrasound waves, to the ultrasound transmission and heating body 67. The energy converted into heat heats the ultrasound transmission and heating body 67 to the already indicated temperature, which is above the normal temperature present at the skin surface. The temperature of the ultrasound transmission and heating body 67 is detected by the electrode 64, also acting as a temperature sensor, in cooperation with the temperature measuring device 97. This latter device supplies the microprocessor of the evaluation and control device 93 with a digital signal representing the value of the temperature. The device 93 regulates the ultrasound generator 96 in such a way that the measured temperature is kept at a predetermined command value. The regulation of the temperature may be done by pulse width regulation of the ultrasound wave pulses that are generated, for example.

The heated ultrasound transmission and heating body 67 supplies heat to the skin 3 by heat conduction. Ultrasound waves are also transmitted to the skin and absorbed in it. This absorption takes place above all in the blood-supplied layers of the skin that contain living cells, so that internal layers of the skin are heated directly by the ultrasound waves. Both the heat conduction and the ultrasound wave transmission take place in part through the light sources, light receivers and light guide means. In addition, the heat created from electrical energy in the light sources and the light receivers may also contribute to heating of the skin. The continuous heating of the skin by heat conduction and by ultrasound waves absorbed in the interior of the skin makes it possible to heat the skin zone used for measuring the oxygen saturation to a relatively high, rather uniform temperature that promotes profusion, without any region of the skin being damaged by overheating. Since the block, which comprises the ultrasound transmission and heating body 67 and the components embedded in it, extends as far as the plane defined by the housing rim 25a, it is not necessary for measurement to introduce any such material or any other material whatever serving to transmit ultrasound, whether semi-solid or somewhat flowable or liquid, into any voids, besides the aforementioned thin layer of polyethylene glycol to be disposed between the sensor and the skin. Using the sensor 23 is therefore quite simple, and in particular is simpler than the use of the sensors commented on in the introduction and known from U.S. Pat. No. 4,890,619.

The third type of light, or in other words the green light generated by the third light source 31, having a wavelength of approximately 575 nm, is absorbed relatively strongly by hemoglobin that lacks oxygen, hemoglobin that contains oxygen, and hemoglobin that contains carbon monoxide. The light absorption coefficients of hemoglobin with and without oxygen also have rather similar variables at this wavelength. The ratio between the amplitude of the intensity of the scattered light of the third light type, varying periodically over time at the rate of the pulse frequency, and the maximum or mean or minimal value of the intensity of the total scattered light of the third type of light therefore provides a measure for the relative magnitude of the volume of blood present in the particular portion of the skin penetrated by the light, and this measure is largely independent of the saturation of the hemoglobin. The evaluation and control device 93 is embodied to detect this last-mentioned ratio. Optionally, on the basis of formulas ascertained by model calculations and/or value relationships and calibrations stored in table form, the device 93 can determine from the aforementioned ratio absolute values for the ratio between the blood volume and the total volume of the portion of skin involved. Ascertaining the variable that provides a measure of the blood volume can be done with or without heating of the skin, selectively.

Furthermore, preferably also for the third type of light, only that light which passes through the evaluation zone selected for determining the oxygen saturation to reach the sensor is evaluated to determine the blood volume.

The display device 76 shows the oxygen saturation value sa, the pulse frequency p, and a value bv that provides a measure for the blood volume.

The switch and/or control devices 77 make it possible to feed in at least one upper and/or lower limit value for the oxygen saturation value, and optionally for other measured variables as well. If such a limit value is exceeded or fails to be obtained, this can then be signaled optically by the display device 76 and/or acoustically by the acoustic alarm.

The system 21 is calibrated by the manufacturer before shipment. Under some circumstances, however, the intensities of the light pulses generated by the three light sources, or the sensitivities of the various light receivers for the various light wavelengths may change. The term sensitivity is used here to mean the ratio between the level of the electrical voltage pulse generated by a light receiver and the intensity of a pulse of light reaching the light receiver.

If the sensor 23 is not used for measurement, it can be temporarily retained in the indentation 82a of the supports 82 of the calibration light distributor 81. The light transmission sites 35 and light reception zones 45 of the sensor 23 are then oriented toward the light coupling elements 85 and 86, respectively, of the calibrating light distributor 81, and may for instance rest on them. A user can then put the electronic circuit means into a calibration mode by manual actuation of at least one of the switch and/or control devices 77. In this mode, the evaluation and control device 93 controls the light source power device 94 in such a way that each of the three light sources 31 generates at least one light pulse. Some of the light transmitted out of the sensor at the light transmitting sites 34 is then distributed by the calibrating light distributor 81 to the various light admission fields 44 or light reception zones 45 of the sensor and delivered there to its light receivers 41. Each light receiver then generates one voltage pulse for each of the three types of light. The heights—in other words the voltage values—of these pulses and/or values derived from them by the microprocessor are then stored as calibrated values in memory locations of a memory belonging to the evaluation and control device 93, until the next calibration. After the calibration, the system 21 can be put into the normal operating mode by manual actuation of at least one of the switch and/or control devices 77 or by means of a switch device actuated by the removal of the sensor 23 from the support 82. In that mode, the newly ascertained and calibrated values are then employed for evaluating the measured light intensity values. By means of such calibrations, it can be assured that even after long use, the system 21 will soon furnish accurate measurement results.

Figure 7:
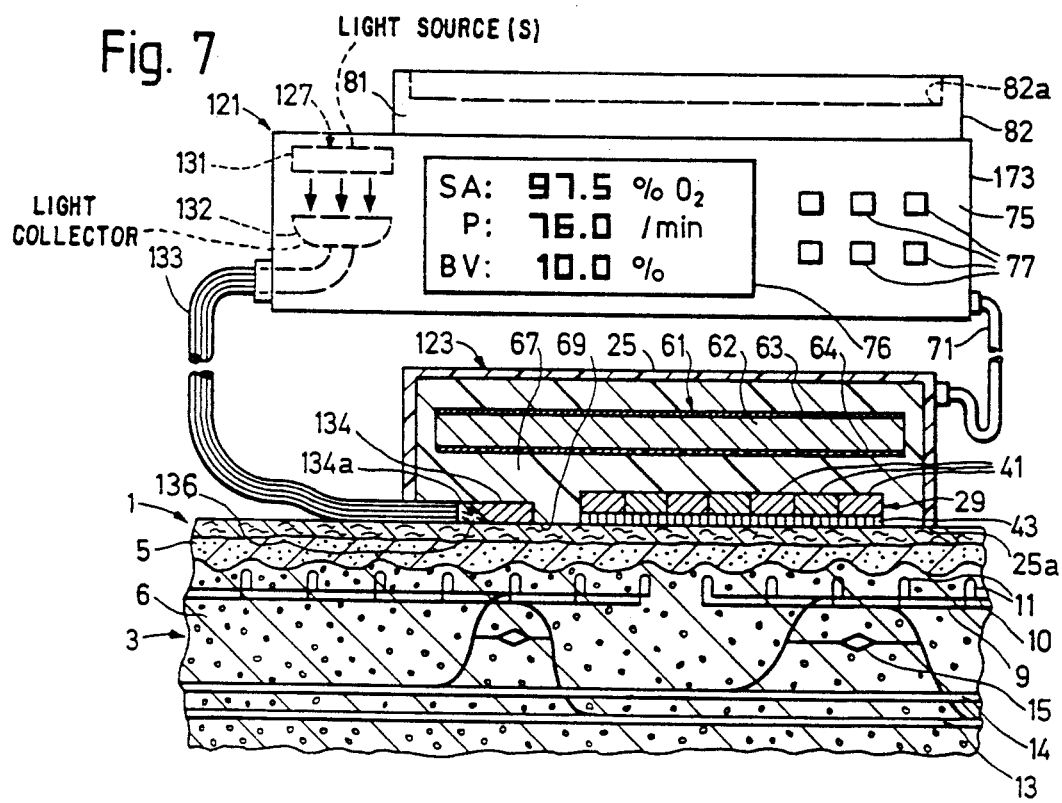
FIG. 7 is a view corresponding to FIG. 1 of a variant of the system.

The system 121 that can be seen in FIG. 7 has a sensor 123, partly corresponding to sensor 23, and a measuring instrument 173 partly corresponding with the measuring instrument 73. If not stated otherwise hereinafter, the two systems may be embodied similarly; parts corresponding to one another are identified by the same reference numerals. However, the system 121 has light transmitting means or light radiating means 127, which are embodied differently from the light transmitting means 27 of the system 21. To generate light of the various types of light needed, the light transmitting means 127 have at least one light source 131 disposed outside the sensor 123 in the housing 75 of the measuring instrument 173. The light transmitting means 127 may, for example, similarly to the light transmitting means 27, have a plurality of light sources, each comprising a semiconductor diode, and by each of which light of a different wavelength is generated. If the light source 131, or each light source 131, during operation generates light at different wavelengths that is, over a wide spectrum—the light transmitting means may also have at least one interference filter separate light have precisely the desired wavelength for each type of light from the spectrum.

The measuring instrument 173 also has a light collector 132, in order to collect the light generated by the at least one light source 131 and deliver it to the one end, retained in and/or on the housing 75, of elongated flexible light guide means 133, which have at least one glass fiber. The other end of the light guide means 133 is connected to the sensor 123. On its side that rests on the body 1 during measurement, this sensor may for instance have a groove in which the aforementioned second end of the light guide means 133 and a metal reflector 134 are disposed, the reflector having a reflector face 134a that is inclined by 45° from the side of the sensor resting on the body 1 and is oriented toward the end of the light guide means 133. Together with the reflector 134, the light guide means 133 define a light transmitting zone 135, visible in FIG. 8, in which the light can be transmitted out of the sensor 123 and into the body 1. The interstice present between the reflector 134 and the end of the light guide means 133 secured in the sensor is filled with a light-transmissive material 136. The light collector 132, the light guide means 133, the reflector 134 and the material 136 together form light transmitting means, with which the light generated by the at least one light source 131 can be transmitted to the light transmitting zone 135. In operation of the system 121, the light of all the types of light generated can be transmitted out of the sensor 123 sequentially at one and the same light transmitting site—in other words through one and the same face of the light transmitting zone 135. The light transmitting zone 135 may for instance be circular, as seen in a plan view on the side of the sensor resting on the body 1 during measurement, and in this plan view it may have a very short length in all directions, preferably no more than 2 mm, for instance no more than 1 mm, or even only no more than 0.5 mm. Furthermore, the light guide means 133, like the photoconductive means 33, have an effect that aligns the light rays more or less parallel and collimates them.

Figure 9:
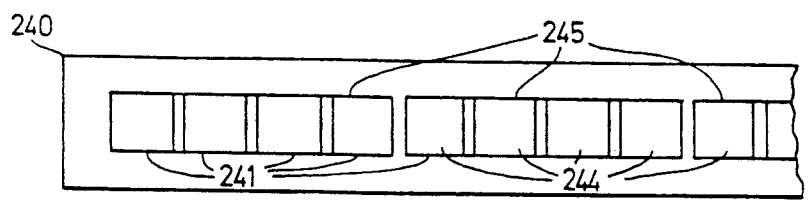
FIG. 9 is a plan view of an integrated circuit having a plurality of photodiodes used as light receivers.

In the systems 21 and 121, the light receivers 41, comprising separate photodetectors, may be replaced by an integrated circuit, as schematically shown at 240 in FIG. 9. The integrated circuit 240 has a straight line of photo-semiconductors, namely photodiodes, each of which forms one light receiver 241. The sensor containing the integrated circuit 240 may, for example, also have light guide means 43 not shown in FIG. 9, which are disposed in a manner analogous to that in the systems 21 and 121. Each light receiver 241 defines one light admission field 244, on the side of the sensor that rests on the body to be examined during measurement. The light admission fields 244 may, for example, be square or rectangular and may be separated by narrow interstices. The integrated circuit 240 may under some circumstances include a relatively large number of photodiodes, for example amounting to at least 100. The microprocessor of the electronic circuit means connected to the integrated circuit can therefore be embodied, for example, for adding together the light intensities, measured in each case by a group of light receivers 241 in succession in the longitudinal direction, before or after the cumulative filtration, and assign one light reception zone 245 to each of these groups. All the light reception zones 245 may have an equally large number of light admission fields 244. In the use of the sensor containing the integrated circuit 240, the light intensities are first measured separately in each light reception zone 245. Then, similarly to the system 21, one of the light reception zones 245, for example, is selected as an evaluation zone, and the light reaching the sensor there, or that has reached the sensor there is evaluated to determine the oxygen saturation. However, to determine the oxygen saturation, the microprocessor ma also add together the light intensities measured by two or more groups of light receivers, and accordingly during measurement vary the size of the evaluation zone in which the light is evaluated, in a manner analogous to what has already been described for the light receivers 41.

The systems may also be designed for other types and/or modified. For example, the systems may be embodied to detect and display the carbon monoxide saturation of the blood as well. The carbon monoxide saturation can be ascertained, for instance, from the intensity ratio between the third and second types of light. To determine the carbon monoxide saturation, it is optionally also possible to generate and measure pulses of light of a fourth type, having a wavelength that is shorter than that of the first, second and third types of light. The carbon monoxide saturation can be measured by the evaluation of the intensities of light that reaches the sensor in the same evaluation zone as the light evaluated to determine the oxygen saturation. The value of the measured carbon monoxide saturation may be displayed in percent, for example.

The possibility also exists, however, of providing light transmitting means which in operation transmit light in only two different wavelengths into the body of a patient to be examined. Moreover, especially if the light sources are disposed outside the sensor, they may comprise other types of lasers, instead of the light emitting or laser diodes already mentioned.

The light guide means 33, 43 may be replaced with light guide means that instead of flat glass plates have a cluster of short fiber segments, disposed next to one another and cemented together or firmly joined in some other way, which fibers serve as optical waveguides. Such light guide means then provide a collimation that is rotationally symmetrical to the axes of fibers. In addition, the light guide means 33, along with the photoconductive means 43, may be formed from a single coherent, chip-like body having plates or fibers of glass.

The light guide means 33 located in front of the light sources 31 may also be formed by a single piece of glass, for instance of chip form. With this kind of embodiment of the light guide means 31, it is advantageous to mirror-coat the peripheral faces of the piece of glass, and/or to form the ultrasound transmission and heating body 67 surrounding the peripheral faces from an opaque cast resin.

The light reception means may optionally be equipped with two or three or possibly even more rows of light receivers disposed side by side. The light guide means belonging to the light reception means may then, for one of the rows of light receivers, have plates disposed as in FIG. 3, perpendicular to the skin surface, and serving as optical waveguides, or may have glass fibers that are perpendicular to the skin surface. The light guide means assigned to the other light receivers, contrarily, may have plates or fibers that in a sectional or projection plane parallel to the sectional plane of FIG. 1 form an angle with the skin surface and the straight line 47 that differs from 90° and may tilt to the left away from the skin surface—in other words toward the light sources. If a total of three rows of light receivers are present, then the angle formed by the plates or fibers with the straight line 47 in a sectional or projection plane parallel to the sectional plane of FIG. 1 may for example be 90° for one row, approximately 25° to 45° in another row, and approximately 50° to 70° in the last one. Optionally, a row of light receivers may also be provided to which light guide elements are assigned that have plates or fibers inclined to the right away from the skin surface in a section corresponding to FIG. 1; the angle formed with the straight line 47 should be at least 60°. If the light guide means belonging to the light reception means have plates or fibers that form different angles with the straight line 47 and the skin surface, the evaluation and control device 93 may be embodied, for ascertaining the oxygen saturation, so as to select an evaluation zone having at least one light reception zone, in which both the spacing from the light transmitting zone and the primary admission direction of the light guide means that is, the angle of the optical wave guide with the skin surface and the straight line 47—is most favorable.

Optionally, in the system 21 it is possible to dispense with light guide means 33, and/or in the systems 21, 121, the light guide means 43 can be dispensed with.

Figure 8:
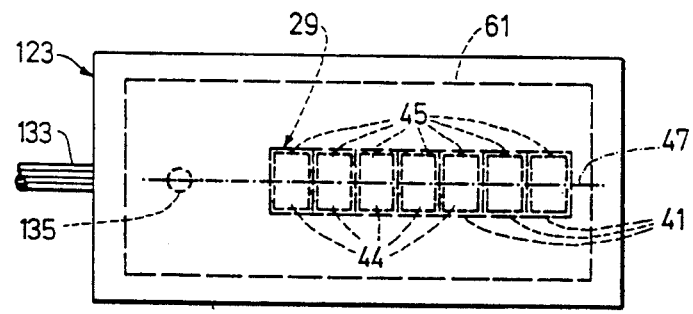
FIG. 8 is a plan view of the sensor on the system shown in FIG. 7.

The light receivers and the light reception zones may be curved concentrically with the center of the light transmitting region, in a projection corresponding to one of FIGS. 2 or 8 and at right angles to the skin surface, and may have the form of circular rings that may extend over the same central angle. The possibility also exists of providing light receivers disposed on both sides of the light transmitting zone and in mirror symmetry with respect to it, in terms of a plan view corresponding to one of the FIGS. 2 or 8.

It would also be possible to accommodate the light receivers outside the sensor in the housing 75 and to connect them by flexible optical waveguides with the light admission fields or light reception zones of the sensor. It would also even be possible optionally to provide only a single light receiver, which can be connected optically to the various light admission fields or light reception zones in alternation via a controllable optical shunt or switch device.

It is also optionally possible to embody the side of the sensor resting on the body 1 during measurement as curved in slightly concave fashion rather than being flat in a sectional plane; the radius of curvature may be at least, or approximately 50 cm, for instance. This allows the sensor to rest well on a convex surface of the body of the patient to be examined. The row formed by the light admission fields and light reception zones should then preferably still be straight, when seen in a plan view on the side of the sensor that rests on the body to be examined in measurement. The sensor may possibly even be slightly flexible, so that its side or face resting on the body to be examined during measurement can adapt to the surface of the body.

The ultrasound source 61 may possibly be omitted.

The calibrating light distributor may have, instead of optical waveguides, at least one light reflector and/or one light scattering device, in order to distribute light, shone toward it by the light transmitting means, to the light admission fields and light reception zones of the sensor. A light scattering device may for example have a body with a matrix of glass, in which a number of small particles effecting light scattering, comprising a different glass or some other material are disposed.

It will be understood that the above description of the present invention is susceptible to various modifications, changes and adaptations, and the same are intended to be comprehended within the meaning and range of equivalents of the appended claims.

What is claimed is:

1. A system for measuring a saturation of at least one gas in blood present in a living body, comprising: light radiating means for generating light having various wavelengths; a sensor intended to rest on the body, the sensor having a light radiating zone where the light having various wavelengths is emitted from the sensor into the body, and light receiving zones located at various distances from the light radiating zone; light receiving means for detecting the intensity of light which is scattered back by the body and which reaches each light receiving zone; and circuit means, connected to the light receiving means, for detecting the at least one gas saturation from light intensities detected for the various wavelengths, the circuit means including selection and evaluation means for selecting one evaluation zone among the light receiving zones on the basis of a predetermined criterion, and for evaluating light reaching the light receiving means only in the selected evaluation zone in order to detect the at least one gas saturation.

2. The system of claim 1, wherein the selection and evaluation means comprises means for evaluating a portion of the received light that varies periodically over time with the pulse frequency of the blood flowing through the body in order to detect the at least one gas saturation and to determine the evaluation zone in such a way that the evaluation zone includes a light receiving zone in which the amplitude of the intensity of said portion of the received light that varies periodically over time, having one of the wavelengths, is greatest.

3. The system of claim 1, wherein the light receiving means comprises a plurality of light receivers for separate measurement of the intensities of the light reaching them, at least one light receiver being associated with each light receiving zone; and wherein the selection and evaluation means comprises means for assigning at least one and at most some of the light receivers to the evaluation zone.

4. The system of claim 1, wherein the sensor has at least three light receiving zones which are at various distances from the light radiating zone.

5. The system of claim 4, wherein the light receiving zones form a row that is straight, as seen in a plan view of a side of the sensor intended for resting on the body; wherein each light receiving zone has at least one light admission field, through which light can enter the light receiving means; and wherein the length of each light admission field measured in a longitudinal direction of the row amounts to more than half the distance between the center point of adjacent light admission fields.

6. The system of claim 5, wherein the length of the light radiating zone, measured parallel to the longitudinal direction of the row of light receiving zones, is at most 2 mm.

7. The system of claim 1, wherein the light radiating means comprises light sources, disposed in the sensor, for generating the light having the various wavelengths.

8. The system of claim 1, wherein the light radiating means comprises at least one light source disposed outside the sensor to generate the light having various wavelengths, and further comprising light transmitting means for connecting the at least one light source to the sensor in such a manner that the various wavelengths of light are transmitted sequentially out of the sensor through a single surface of the light radiating zone.

9. The system of claim 1, wherein the light radiating means comprises at least one light source, and light guide means disposed between the at least one light source and the light radiating zone.

10. The system of claim 9, wherein the light radiating zone and the light receiving zones have center points that are located on a center line that is straight, in a plan view of a side of the sensor intended to rest on the body, and wherein the light guide means comprises optical waveguides, formed from flat plates disposed in the sensor, which waveguides are perpendicular to the center line in the aforementioned plan view.

11. The system of claim 1, wherein the light receiving means comprises light receivers and light guide means between the light receiving zones and the light receivers.

12. The system of claim 11, wherein the light radiating zone and the light receiving zones have center points that are located on a center line that is straight, in a plan view of a side of the sensor intended to rest on the body, and wherein the light guide means comprises optical waveguides, formed from flat plates disposed in the sensor, which waveguides are perpendicular to the center line in the aforementioned plan view.

13. The system of claim 1, wherein the body has a pulse with a pulse duration period, and wherein the selection and evaluation means comprises means for dividing the pulse period duration into a plurality of time intervals, and for accumulating during a plurality of pulse periods the intensities of the light detected by the light receiving means during the plurality of time intervals, separately for the various wavelengths.

14. The system of claim 1, wherein the sensor comprises at least one ultrasound source and ultrasound transmission means for transmitting ultrasound waves generated by the ultrasound source to the living body, the ultrasound transmission means including an ultrasound transmission body which forms a contact face intended for resting on the living body and which substantially surrounds the light radiating zone and all the light receiving zones.

15. The system of claim 14, wherein the ultrasound transmission body converts 30% to 70% of the energy delivered to it in the form of ultrasound waves into heat and transmits it to the living body at least partly by heat conduction.

16. The system of claim 14, wherein the at least one ultrasound source has an electrode, which also serves as an electric resistor that acts as a temperature sensor.

17. The system of claim 1, further comprising a calibration light distributor which receives the sensor during a system calibration procedure, the calibration light distributor comprising means for distributing light emitted from the light radiating zone of the sensor to the light receiving zones of the light receiving means.

18. The system of claim 1, wherein the light radiating means comprises means for generating at least three types of monochromatic light, each having a different wavelength, one of the types of light having a wavelength of 500 nm to 600 nm and serving to detect a variable which provides a measure of the volume of blood present in a portion of the living body.

19. The system of claim 1, wherein the at least one gas comprises oxygen, and the system measures the oxygen saturation of blood.

20. The system of claim 1, wherein the selection and evaluation means comprises means for evaluating a portion of the received light that varies periodically over time with the pulse frequency of the blood flowing through the body in order to detect the at least one gas saturation and to determine the evaluation zone in such a way that the evaluation zone includes a light receiving zone in which the ratio of the amplitude of the intensity of said portion of the received light that varies periodically over time, having one of the wavelengths, and one of the maximum, mean, and minimum value of the total light which has said one of the wavelengths and which is received at the respective light receiving zone, is greatest.

* * * * *